United States Patent [19]

Milligan et al.

[11] Patent Number: 4,533,765

[45] Date of Patent: Aug. 6, 1985

[54] POLYHYDROXY AROMATIC COMPOUNDS FROM ALKALI METAL HYDROXIDE AND MONONUCLEAR AROMATIC COMPOUNDS

[75] Inventors: Barton Milligan, Coplay; George B. DeLaMater, Macungie, both of Pa.

[73] Assignee: Air Products and Chemicals, Inc., Allentown, Pa.

[21] Appl. No.: 559,078

[22] Filed: Dec. 7, 1983

[51] Int. Cl.$^3$ .................... C07C 37/00; C07C 39/10
[52] U.S. Cl. ................................. 568/763; 568/716
[58] Field of Search ............... 568/730, 763, 769, 716, 568/764

[56] References Cited

U.S. PATENT DOCUMENTS

| | | | |
|---|---|---|---|
| 2,736,752 | 2/1956 | Hoffmann et al. | 568/763 |
| 3,230,266 | 12/1983 | Baldoni et al. | 260/621 |
| 3,520,940 | 7/1970 | Smith | 568/763 |
| 4,172,960 | 10/1979 | Baldwin et al. | 568/772 |

FOREIGN PATENT DOCUMENTS 2362694  6/1974  Fed. Rep. of Germany ...... 568/763

*Primary Examiner*—Werren B. Lone
*Attorney, Agent, or Firm*—Russell L. Brewer; James C. Simmons; E. Eugene Innis

[57] ABSTRACT

This invention pertains to a process for preparing polyhydroxy aromatic compounds by reacting an alkali metal hydroxide with a hydroxymononuclear aromatic compound, e.g., phenol or resorcinol. The reaction is carried out in the presence of a metallic hydrogenation catalyst, suitably nickel, or cobalt, the metal being present in an amount sufficient for catalyzing the reaction. The polyhydroxy aromatic compound is then formed by adding a protonating agent to the reaction product, with the protonating agent liberating the hydroxy compound from the salt.

6 Claims, No Drawings

POLYHYDROXY AROMATIC COMPOUNDS FROM ALKALI METAL HYDROXIDE AND MONONUCLEAR AROMATIC COMPOUNDS

DESCRIPTION OF THE PRIOR ART

The production of polyhydroxy mononuclear aromatic compounds has been under study for decades. One technique has been to disulfonate benzene and then effect caustic fusion of disulfonated product to produce the sodium salt of resorcinol. Another is to synthesize m-diisopropyl benzene and autooxidize to the bishydroperoxide intermediate. Decomposition of the intermediate under acidic conditions results in resorcinol.

Another technique for producing polyhydroxy aromatics is shown in U.S. Pat. No. 3,230,266. It discloses a technique for producing phloroglucinol by reacting tetrahalobenzene, e.g. tetrachlorobenzene with ammonia in the presence of a cuprous salt and then protonating the reaction mixture by addition of acid.

Barth et al. in *Ann.der Chemie*, 156,93 (1870) discloses the preparation of resorcinol by fusion of phenol with potassium or sodium hydroxide.

SUMMARY OF THE INVENTION

This invention relates to a process for forming a polyhydroxy aromatic compound by directly hydroxylating a hydroxymononuclear aromatic compound via direct nucleophilic substitution of the hydrogen atom on the aromatic ring. The direct hydroxylation is carried out by reacting a hydroxymononuclear aromatic compound with an alkali metal hydroxide in the presence of a nickel or cobalt hydrogenation catalyst, the catalyst being present in an amount sufficient for catalyzing the reaction under the conditions utilized. The polyhydroxy composition then is liberated from the intermediate reaction product by adding a protonating agent such as a mineral acid.

Some of the advantages of the process are:

it provides a direct method for preparing polyhydroxy aromatic compositions since the process involves direct nucleophilic displacement of a hydrogen atom as opposed to nucleophilic displacement of intermediate groups, such as, halogen, nitrogen, and sulfonic acid;

it provides an ability to produce polyhydroxy compounds of polynuclear compositions, e.g., biphenols;

it offers efficiency in terms of raw materials; and it is energy efficient.

DETAILED DISCRIPTION OF THE INVENTION

A procedure has been developed which permits the direct substitution of a hydroxy group on an hydroxyaromatic compound as compared to the usual nucleophilic substitution of the hydroxy group for a halogen atom, sulfonate, or sulfinic group pendant the aromatic ring as performed by the prior art. In accordance with this invention, the polyhydroxy aromatic compounds are produced by effecting a catalytic reaction between a mononuclear aromatic composition and an alkali metal hydroxide. A catalyst is necessary since the alkali metal hydroxide and hydroxymononuclear aromatic composition, by themselves, are relatively unreactive and this unreactivity has been observed in the art. Examples of hydroxymononuclear aromatic compounds suited for practicing invention include phenol or resorcinol or substituted derivatives.

The hydroxyl functionality is supplied to the mononuclear aromatic compounds via an alkali metal hydroxide which, includes lithium hydroxide, potassium hydroxide or sodium hydroxide. These metal hydroxides are sufficiently reactive to effect nucleophilic substitution of the hydrogen atom on the aromatic ring. Other hydroxides such as ammonium hydroxide and the alkaline earth metal hydroxides are not sufficiently reactive.

In order to effect reaction between the alkali metal hydroxide and hydroxymononuclear aromatic compound, a catalytic material must be present in the reaction system in an amount sufficient to catalyze the formation of an intermediate reaction product. Although a specific analysis of the reaction product has not been made, it is believed that the reaction product is an alkali metal salt of a hydroxy aromatic. This belief is based upon the fact that upon addition of a protonating agent the polyhydroxy composition is liberated.

Catalysts suitable for effecting the reaction are hydrogenation catalysts such as cobalt and nickel. As with conventional hydrogenation catalysts, these hydrogenation metals may be carried upon a support. However, the support should be stable under the reaction conditions. The metal catalyst used in the reaction system is provided in the amount sufficient to catalyze a reaction in the conditions set forth. Generally, this amount is from 0.1-5% by weight of the alkali metal hydroxide.

The alkali metal hydroxide is incorporated into the reaction medium in at least a stoichiometric quantity for effecting nucleophilic displacement of the hydrogen ion with the hydroxy group. Generally, quantities from one to five moles excess alkali metal hydroxide per one mole quantity of hydroxymononuclear aromatic compound are utilized. Selectivity to resorcinol is better at high mole ratios than at at lower ratios.

The temperature used in carrying out the reaction to the intermediate is that temperature necessary to effect the formation of the intermediate reaction product, which is generally from 300° to 400° C. Under some circumstances, results are improved if the reaction is carried out under reduced pressures. Higher pressures do not significantly enhance the reaction.

After the initial reaction between the alkali metal hydroxide and hydroxymononuclear aromatic compound, the reaction product is contacted with a protonating agent to liberate the hydroxyl group. Typical protonating agents suited for converting the intermediate product to the polyhydroxy composition include aqueous mineral acids, such as, sulfuric or hydrochloric acid. The protonating agent is added in an amount sufficient to convert the reaction product to the hydroxy composition. Sufficient protonating agent to neutralize any excess base and to protonate the product is required. Liberation of the hydroxy or polyhydroxy compound is readily effected at temperatures from 10° to 50° C. and atmospheric pressure.

In many instances it is preferable to separate the intermediate reaction product, i.e., the salt from the reaction medium prior to adding the protonating agent. This separation is desirable, otherwise the system would inherently contain large amounts of alkali metal hydroxide, which must be neutralized before the salt can be protonated. To avoid neutralizing all of the excess alkali metal hydroxide, it is necessary to convert the reaction product to a water insoluble, organic soluble system which then can be separated from the reaction mixture by addition of the hydroxyl compound. Then, when the protonating agent is added the product returns to the aqueous phase. Ion pair extraction is one technique which is well suited to the production of resorcinol, which is obtained by the reaction of sodium phenoxide, with sodium hydroxide. Ion pair extraction is effected by combining tetrabutyl ammonium ion or similar species, as the extractant and chlorobenzene or anisole as a solvent. Addition of sulfuric acid converts the salt to resorcinol plus tetrabutylammonium hydrogen sulfate.

The following examples are provided to illustrate various embodiments of the invention.

EXAMPLE 1

A mixture of five parts by weight of sodium hydroxide and one part by weight of phenol dissolved in a minimum amount of water was stirred together until all of the phenol had been converted to its sodium salt. Then a solution of nickel (II) nitrate was added, the quantity of nickel ion being 0.01 mole per mole of phenol. This mixture was heated under vacuum (about 1 mm Hg) in a platinum crucible at about 150°–200° C. until all of the water was removed and then heated to 395° C. for two hours while still under vacuum. Shortly before the melting point of the mixture was reached, the green color of the nickel turned black indicating that the nickel had been reduced to nickel metal or converted to a black oxide. As soon as the mixture melted, evolution of gas began and continued during the entire heating period. After cooling to room temperature, the mixture was dissolved in water, and the solution was adjusted to pH 7 with sulfuric acid. After thorough extraction with ether, the pH of the solution was lowered to 2, and another extraction with ether was conducted. The ether extracts were dried and then evaporated to dryness. The residue of the extract at pH 7 weighed 1.20 times the weight of the phenol charged while the pH 2 residue weighed 0.05 times the weight of phenol charged. Thin layer chromotograms (TLC) of the pH 7 residue showed that 40% of the phenol charged remained and that resorcinol, 3,3'-biphenol (3,3'-dihydroxybiphenyl), and 2,3'-biphenol in 2.5%, 3.5% and about 1% yields respectively were obtained. The biphenols were identified by comparison of their Rf values and their infrared spectra with authentic samples. A trace of 2,2'-biphenol, identified by its Rf, was also formed. When this experiment is conducted without the nickel catalyst, some gas evolution is observed but much less than that with the nickel, and only traces of the products mentioned are formed.

The experiment was repeated using nickel chloride solution in place of nickel nitrate. A large amount of coke-like material was formed (1.2 parts per part of phenol charged), and only 0.21 parts of material were isolated from the pH 7 extract.

EXAMPLE 2

To test the catalytic activity of various metals, a series of runs comparable to the experiment of Example 1 were made. The temperature was 345° to 350° C. and the time of heating in each was 4 hours. The results were as follows.

| Catalyst Additive | Result |
| --- | --- |
| None (Control) | Very small, almost negligible amounts of resorcinol, 3,3'-biphenol and 2,3'-biphenol were observed by TLC |
| 1% Nickel Nitrate | At least 4–5 times as much resorcinol and biphenols as control was observed |
| 1% Cobalt nitrate | Less Product than obtained with the nickel, smaller proportion of resorcinol |
| 1% Platinum oxide | No change from control |
| 1% Ferric nitrate | No change from control |
| 1% Palladium nitrate | Product was lost but little gas evolution. No apparent change from control |
| 1% Cupric nitrate | No change from control |
| 1% Silver nitrate | No change from control |

EXAMPLE 3

To test the effect of temperature, the experiment of Example 1 was repeated at lower temperatures with increasing times. The products were analyzed by TLC with the sample size being adjusted to give the same size spot for 3,3'-biphenol. The resorcinol spots became smaller as the temperature was lowered showing that the selectivity to resorcinol is best at high temperatures and to biphenols at low temperatures.

| Temperature | Time | Sample Size |
| --- | --- | --- |
| 395° C. | 2 hr | 30 micro grams |
| 365° C. | 2 hr | 40 micro grams |
| 345° C. | 4 hr | 10 micro grams |
| 330° C. | 6 hr | 160 micro grams |
| 300° C. | 7 hr | 160 micro grams |

EXAMPLE 4

The effect of pressure on reaction selectivity can be seen from the following series of reactions, A 1% nickel catalyst was used in each case:

| Pressure | Temperature | Time | Results |
| --- | --- | --- | --- |
| Atm* | 370° C. | 3 hr | Only slight conversion |
| 2 mm Hg | 370° C. | 2 hr | Substantial conversion, higher resorcinol selectivity than atm |
| 2 mm Hg | 330° C. | 6 hr | Lower conversion and lower resorcinol selectivity than 370° C. |
| 10 microns $H_2$ | 310° C. | 2 hr | Higher conversion and resorcinol selectivity was 10 times higher than at 330° C. |

*Swept with nitrogen. In runs swept with air, no products or phenol were found.

EXAMPLE 5

The effect of the ratio of caustic to phenol is shown by the following results obtained in a nickel crucible at 365° C. and about 1 mm Hg pressure.

| Parts NaOH per part phenol | Time | Catalyst | Results (by TLC) |
| --- | --- | --- | --- |
| 1.3 | 3 hr | 1% Ni | 3,3'- & 2,3'-biphenols, trace resorcinol, unidentified products |
| 50 | 2 hr | 2.5% Ni | High selectivity to resorcinol, traces of biphenols and unidentified products |

EXAMPLE 6

The formation of phloroglucinol from resorcinol was observed when resorcinol was substituted for phenol in the procedure of Example 1. The reaction time was 2 hours at 370° C. and 2 mm Hg pressure. The pH 7 extract contained 0.68 gram of aromatics per gram of phenol charged. Analysis by TLC showed that phloroglucinol and an unidentified product were formed at a conversion of approximately 10%. When the TLC plate was sprayed with diazotized benzidine, the phloroglucinol spot was purple and the resorcinol and unknown spots were red. Since products with one hydroxyl group per ring give yellow colors with the same treatment, the unknown product is presumed to be 3,3', 5,5'-tetrahydroxybiphenyl.

EXAMPLE 7

This example shows that resorcinol can be isolated from a large excess of sodium hydroxide without neutralization thereby allowing recycle of excess base and more efficient operation by utilizing the phenomenon of ion pair extraction. A mixture of phenol and resorcinol was prepared to simulate a reaction product from caustic fusion and was dissolved in a minimum amount of water (about 1.3 parts of water per part of combined resorcinol and phenol). This mixture was added to 100 parts of 50% aqueous sodium hydroxide and stirred. A precipitate that formed was found to be the sodium salt of phenol showing that under these conditions unreacted phenol can be separated from product resorcinol by simple filtration.

Then 155 mg resorcinol dissolved in 200 mg of water was added to 15 of 50% sodium hydroxide and 4.0 g of chlorobenzene. After mixing, 950 mg of tetrabutylammonium hydrogen sulfate (2 moles/mole resorcinol) was added. After mixing a white solid, a brownish liquid and a green liquid were present. The solid was found to be sodium sulfate. The brownish aqueous layer was extracted three times with 4.0 g portions of chlorobenzene, and the chlorobenzene solutions were combined. The chlorobenzene extracts were found to contain 27% of the resorcinol charged, and 48% of the resorcinol was found in the original sodium hydroxide solution. Similar results were obtained with anisole as the extracting agent. When ether, methylene chloride of toluene was employed as the extractant, a third liquid layer, which was viscous and green, formed, and little or no resorcinol could be obtained from the solvent layer.

What is claimed:

1. In a process for forming a polyhydroxy aromatic compound by reacting a hydroxymononuclear aromatic compound with a hydroxyl providing agent under conditions effective for forming said polyhydroxy mononuclear aromatic compound, the improvement which comprises:

utilizing resorcinol or phenol as said hydroxy mononuclear aromatic compound;

forming a salt of a polyhydroxy aromatic compound by effecting reaction between said phenol or rescorcinol and an alkali metal hydroxide at a temperature from 300° to 400° C., said reaction carried out in the presence of a nickel or cobalt metallic hydrogenation catalyst, said catalyst being present in an amount effect catalyzing the reaction between the alkali metal hydroxide the phenol or rescorcinol;

adding a protonating agent to the salt of the polyhydroxy aromatic compound in sufficient amount to libera the polyhydroxy aromatic compound.

2. The process of claim 1 wherein said alkali metal hydroxide is represented as a selected from a group consisting of sodium hydroxide, or potassium hydroxide.

3. The process of claim 2 wherein said catalyst is present in proportion of from 0.1 to 5% based upon the weight of said phenol or rescorcinol.

4. The process of claim 3 which includes an additional step of converting the salt of a polyhydroxy aromatic compound to an organic soluble salt, and separating the organic soluble salt from the water soluble material and then protonating the salt.

5. The process of claim 1 wherein said hydroxy mononuclear aromatic compound is resorcinol, and the reaction product after protonation is phloroglucinol.

6. The process of claim 1 wherein said hydroxy mononuclear aromatic compound is phenol and the polyhydroxy reaction product includes biphenol.

* * * * *

UNITED STATES PATENT AND TRADEMARK OFFICE
CERTIFICATE OF CORRECTION

PATENT NO. : 4,533,765

DATED : Aug. 6, 1985

INVENTOR(S) : Barton Milligan and George B. DeLaMater

It is certified that error appears in the above-identified patent and that said Letters Patent is hereby corrected as shown below:

In Column 6, Line 18 should read "in an amount effect<u>ive for</u> catalyzing the reaction"

In Column 6, Line 19 should read "between the alkali metal hydroxide <u>and</u> the phenol"

In Column 6, Line 20 should read "or rescorcinol; <u>and</u>"

In Column 6, Line 23 should read "<u>liberate</u> the polyhydroxy aromatic compound"

Signed and Sealed this

Twentieth Day of May 1986

[SEAL]

Attest:

DONALD J. QUIGG

Attesting Officer

Commissioner of Patents and Trademarks